(12) United States Patent
Simmons

(10) Patent No.: US 9,161,755 B1
(45) Date of Patent: Oct. 20, 2015

(54) METHOD OF REPAIRING AN ANNULUS

(76) Inventor: Edward D. Simmons, Williamsville, NY (US)

( * ) Notice: Subject to any disclaimer, the term of this patent is extended or adjusted under 35 U.S.C. 154(b) by 847 days.

(21) Appl. No.: 12/437,829

(22) Filed: May 8, 2009

Related U.S. Application Data

(60) Provisional application No. 61/126,912, filed on May 8, 2008.

(51) Int. Cl.
| | | |
|---|---|---|
| *A61B 17/04* | (2006.01) | |
| *A61B 17/08* | (2006.01) | |
| A61B 17/122 | (2006.01) | |
| A61B 17/128 | (2006.01) | |
| A61B 17/064 | (2006.01) | |
| A61B 17/068 | (2006.01) | |
| A61B 17/22 | (2006.01) | |

(52) U.S. Cl.
CPC ............. *A61B 17/083* (2013.01); *A61B 17/08* (2013.01); *A61B 17/0487* (2013.01); *A61B 17/064* (2013.01); *A61B 17/068* (2013.01); *A61B 17/122* (2013.01); *A61B 17/128* (2013.01); *A61B 17/1227* (2013.01); *A61B 17/22* (2013.01); *A61B 2017/0645* (2013.01)

(58) Field of Classification Search
CPC ............. A61B 17/064; A61B 17/0643; A61B 17/0644; A61B 17/068; A61B 17/08; A61B 17/083; A61B 17/10; A61B 17/122; A61B 17/1227; A61B 17/128; A61B 17/1285; A61B 2017/00584; A61B 2017/00623; A61B 2017/0618; A61B 2017/0645; A61B 2017/081
USPC ............... 606/139–158, 213, 219–221
See application file for complete search history.

(56) References Cited

U.S. PATENT DOCUMENTS

| | | | | |
|---|---|---|---|---|
| 4,038,987 | A * | 8/1977 | Komiya ...................... 606/142 |
| 4,394,864 | A * | 7/1983 | Sandhaus ..................... 128/843 |
| 5,154,189 | A * | 10/1992 | Oberlander .................. 128/898 |
| 5,618,311 | A * | 4/1997 | Gryskiewicz ................ 606/216 |
| 6,193,733 | B1 * | 2/2001 | Adams ......................... 606/151 |
| 7,473,258 | B2 * | 1/2009 | Clauson et al. .............. 606/139 |
| 7,556,647 | B2 * | 7/2009 | Drews et al. ................. 623/2.11 |
| 2003/0167055 | A1 * | 9/2003 | Kolata et al. ..................... 606/1 |

* cited by examiner

*Primary Examiner* — Dianne Dornbusch
*Assistant Examiner* — Robert Lynch
(74) *Attorney, Agent, or Firm* — Hodgson Russ LLP

(57) ABSTRACT

A repair technique utilizing an elastic loop that is inserted on each side of an annular tear or annular incision following discectomy. The loop is initially an opened linear strand with the open ends inserted on each side of the annular tear with guiding arms in curvilinear fashion. The ends are joined together in the substance of the annulus where the ends are locked under tension. The insertion device is then removed and the elastic loop, which has been under tension, will tighten causing the annular tear to pull together thereby diminishing or eliminating any gap. One or more annular elastic sutures can be used for each annular tear to insure proper closure. The insertion device has guiding arms that push the open ends of the annular suture loop through the substance of the annulus and then forces them together engaging a locking mechanism inside the substance of the annulus. This technique allows for relatively easy and quick repair of the annular defect or tear.

5 Claims, 6 Drawing Sheets

METHOD OF REPAIRING AN ANNULUS

CROSS-REFERENCE TO RELATED APPLICATION

This application claims priority to U.S. Provisional Patent Application No. 61/126,912 filed on May 8, 2008, which is incorporated herein by reference.

FIELD OF THE INVENTION

The present invention relates generally to medical devices and specifically to a medical device for the repair of the annular portion of a disc.

BACKGROUND OF THE INVENTION

A tear in the annular portion of a disc either occurring naturally or as a result of a discectomy may eventually cause herniation or further degeneration of the disc. Accordingly, there is a need for a device and method for repairing the annular portion of a disc.

SUMMARY OF THE INVENTION

The present invention meets the above described need by providing a repair technique utilizing an elastic loop that is inserted on each side of an annular tear or annular incision following discectomy. The loop is initially an opened linear strand with the open ends inserted on each side of the annular tear with guiding arms in curvilinear fashion. The ends are joined together in the substance of the annulus where the ends are locked under tension. The insertion device is then removed and the elastic loop, which has been under tension, will tighten causing the annular tear to pull together thereby diminishing or eliminating any gap. One or more annular elastic sutures can be used for each annular tear to insure proper closure. The insertion device has guiding arms that push the open ends of the annular suture loop through the substance of the annulus and then forces them together engaging a locking mechanism inside the substance of the annulus. This technique allows for relatively easy and quick repair of the annular defect or tear. The locking mechanism may be comprised of a ball and socket that is joined together.

BRIEF DESCRIPTION OF THE DRAWINGS

The invention is illustrated in the drawings in which like reference characters designate the same or similar parts throughout the figures of which.

DETAILED DESCRIPTION

Figure 1:
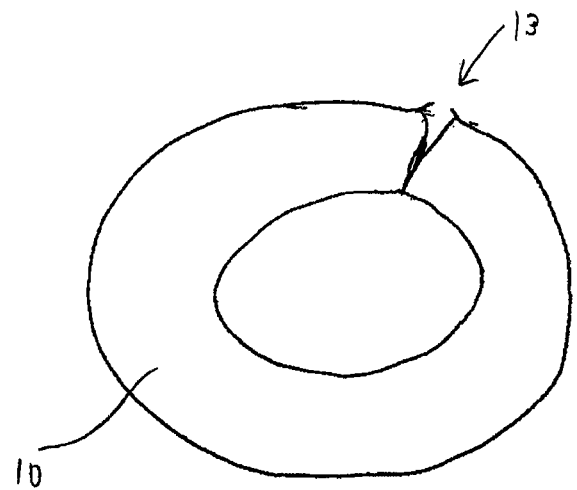
FIG. 1 is a perspective view of an annulus that is torn or an annulus following a discectomy procedure.

Turning to FIG. 1, the annulus 10 of a disc has a tear 13 disposed at its periphery. The tear 13 may occur naturally or may result from an incision during a discectomy. In order to prevent further herniation or damage to the disk, the tear 13 should be closed.

Figure 2:
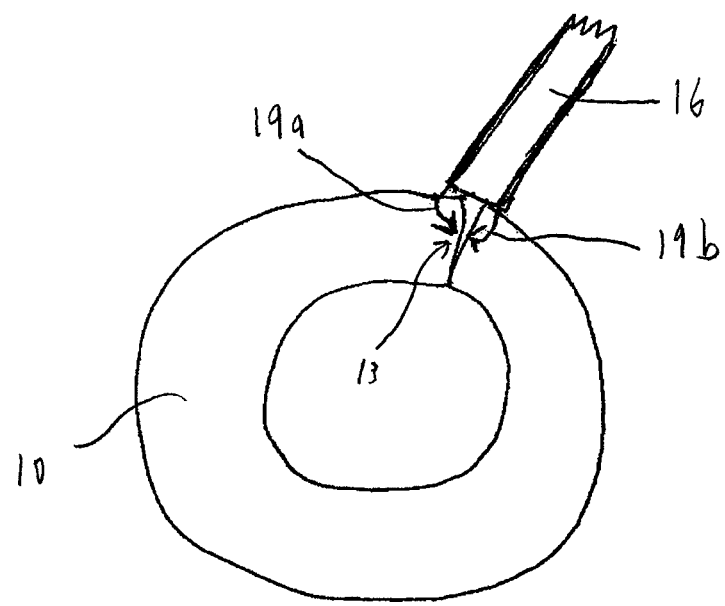
FIG. 2 is a schematic diagram showing the deployment of the suture loop.

As shown in FIG. 2, an insertion device 16 is deployed to the site of the tear 13, and an elastic loop 19 having ends 19a and 19b is deployed through the body of the annulus 10. The elastic loop 19 is deployed under tension and the ends 19a and 19b are connected as described in greater detail herein. Once the insertion device 16 is disengaged from the elastic loop 19, the loop 19 contracts due to its elastic properties and holds the tear 13 closed.

Figure 3:
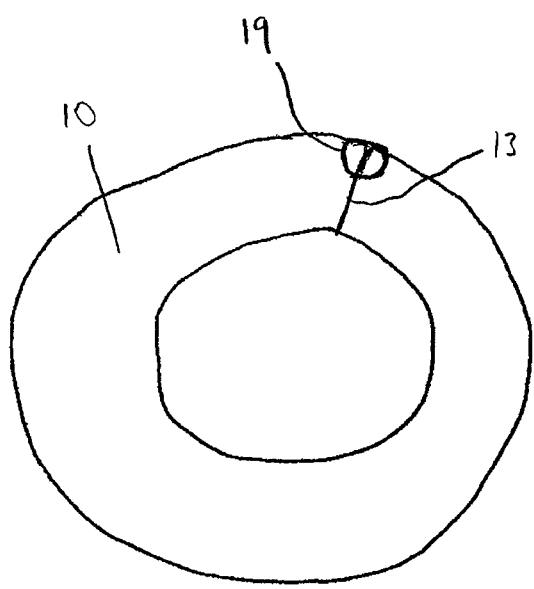
FIG. 3 is a schematic diagram showing the completed insertion of the annular suture in the form of a loop under elastic tension that causes tightening and closure of the annular defect.

Turning to FIG. 3, the tear 13 is repaired and the loop 19 remains installed in the annulus 10.

Figure 4A:
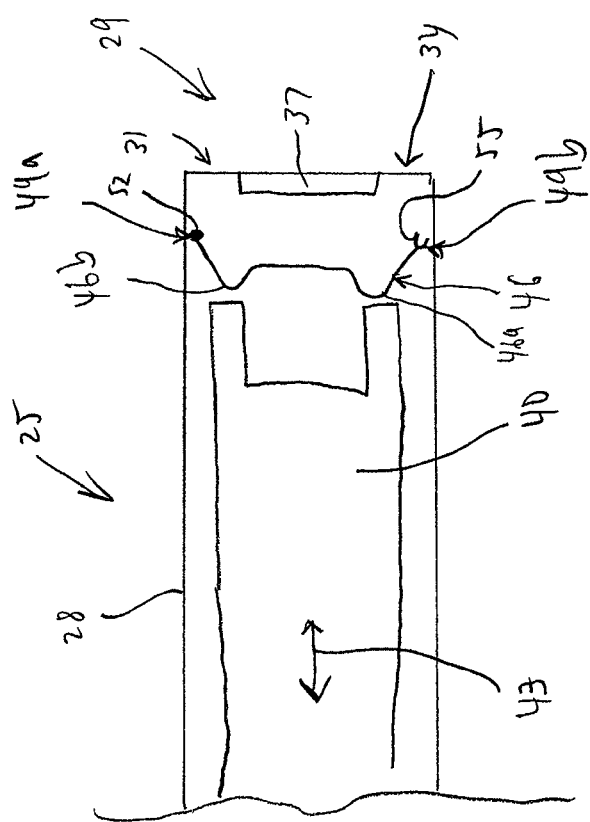
FIG. 4a is partial plan view of a first embodiment of the insertion device.

In FIG. 4a, a first embodiment of the insertion device is shown. Insertion device 25 has an elongate body 28 with a distal end 29 having a pair of openings 31 and 34 on either side of solid member 37 covering the middle of the opening. A sliding member 40 moves inside the body 28 in the direction of arrow 43. The sliding member 40 engages with a pre-formed attachment member 46. The attachment member 46 has arcuate arms 46a and 46b that cause the ends 49a and 49b to be forced together when the attachment member 46 is pushed by the sliding member 40. A ball 52 and socket 55 may be disposed at the ends 49a and 49b. Other locking means will be evident to those of ordinary skill in the art based on this disclosure. When the ends 49a and 49b are pushed together, the ball 52 engages with the socket 55 to lock the attachment member 46 in a loop to hold the tear 13 in a closed position as shown in FIG. 3.

Figure 4B:
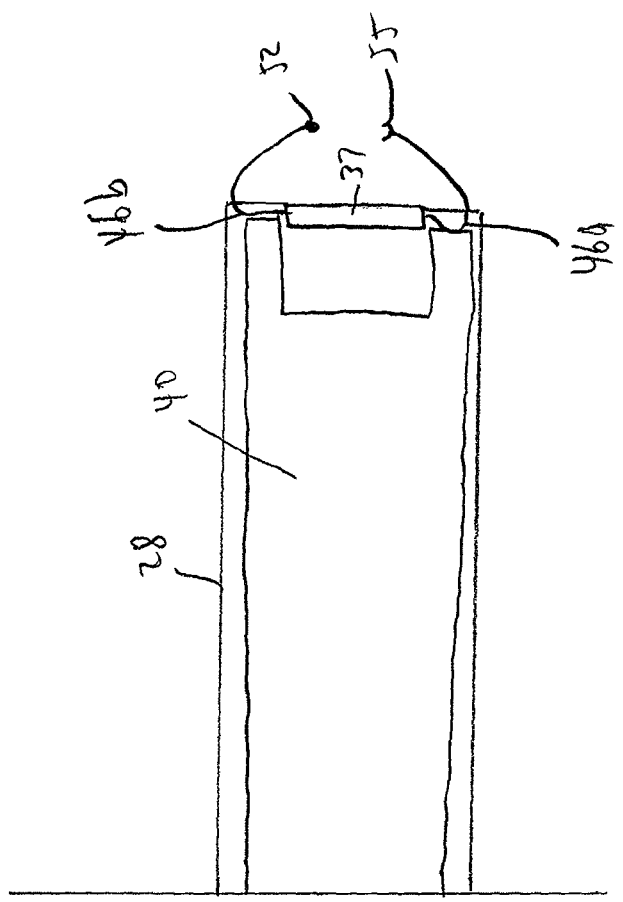
FIG. 4b is a partial plan view of the insertion device of FIG. 4a shown during deployment.

In FIG. 4b, the attachment member 46 is shown during deployment. The attachment member 46 may be constructed of a metal having elastic properties or other material that is suitable for use inside the body. The attachment member 46 is bent from the position shown in FIG. 4a to the position shown in FIG. 4b and the material properties cause the attachment member 46 to retain its shape after being bent. When the sliding member 40 is retracted, the insertion device can be removed from the attachment member 46.

Figure 5:
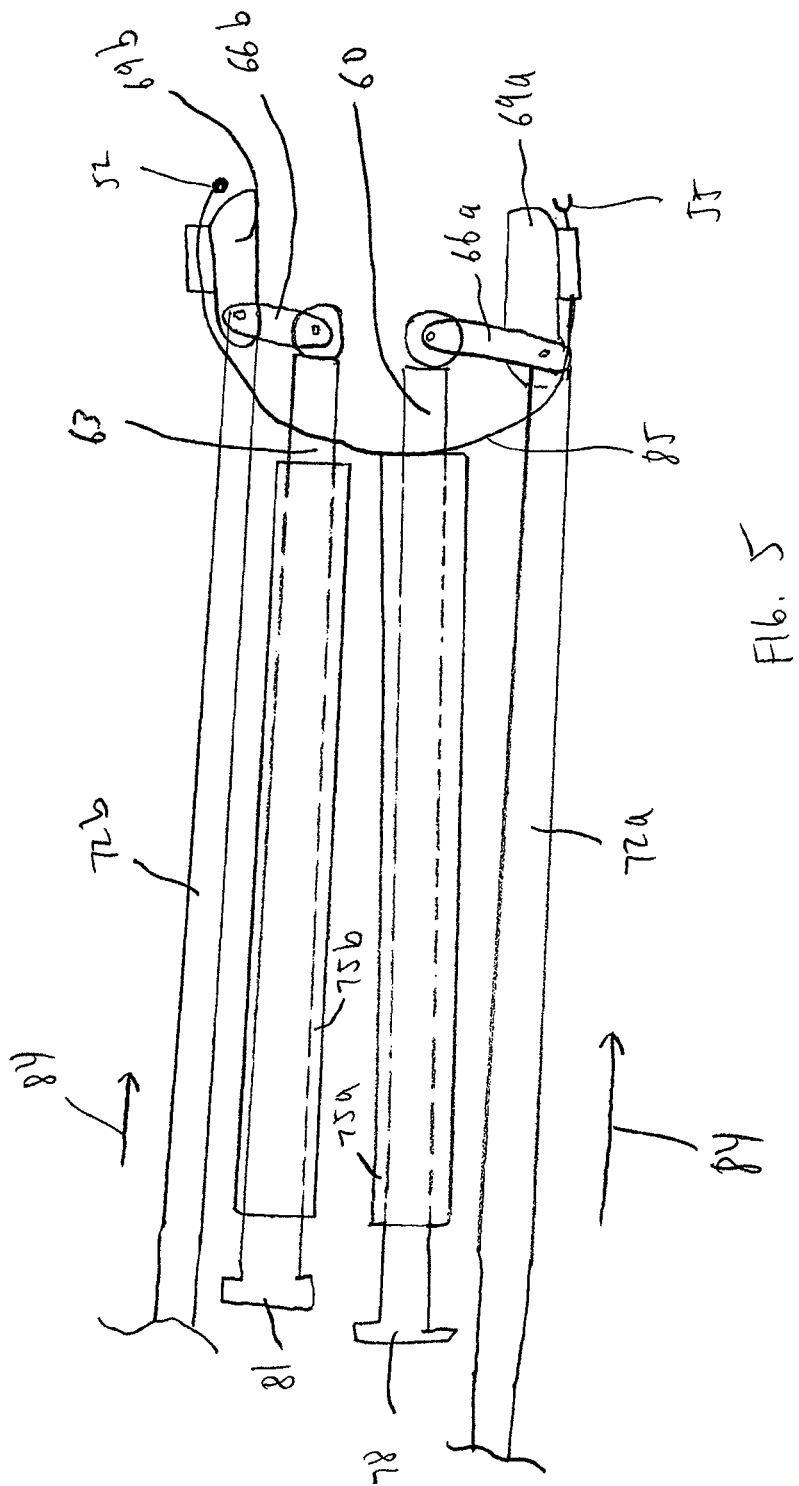
FIG. 5 is a an alternate embodiment of the insertion device.

Turning to FIG. 5, an alternate embodiment of the insertion device includes a pair of sliding link members 60, 63 that are connected to pivoting links 66a and 66b. An elastic, resilient material is used to form a loop. The elastic material is connected to links 69a and 69b by a channel formed in the outside of the links 69a, 69b. The links 69a and 69b are rotatably connected to the sliding link members 60 and 63. A pair of elongate links 72a and 72b are connected to links 69a and 69b. The sliding link members 60, 63 are disposed through sleeves 75a and 75b and the link members 60, 63 have enlarged heads 78, 81 that prevent further motion in the direction of arrow 84. In operation, by pushing the links 72a and 72b in the direction of arrow 84, the links 69a, 69b holding the elastic members 85 are moved forward through the annulus until the enlarged heads 78, 81 engage with the end of the sleeves 75a and 75b. At this point further forward movement of the links 72a and 72b cause the links 66a, 66b to rotate about the end of the sliding link members 60, 63. This causes the ends of the elastic members to rotate toward each other such that the locking members 52, 55 at the end of the elastic members engage.

Figure 6:
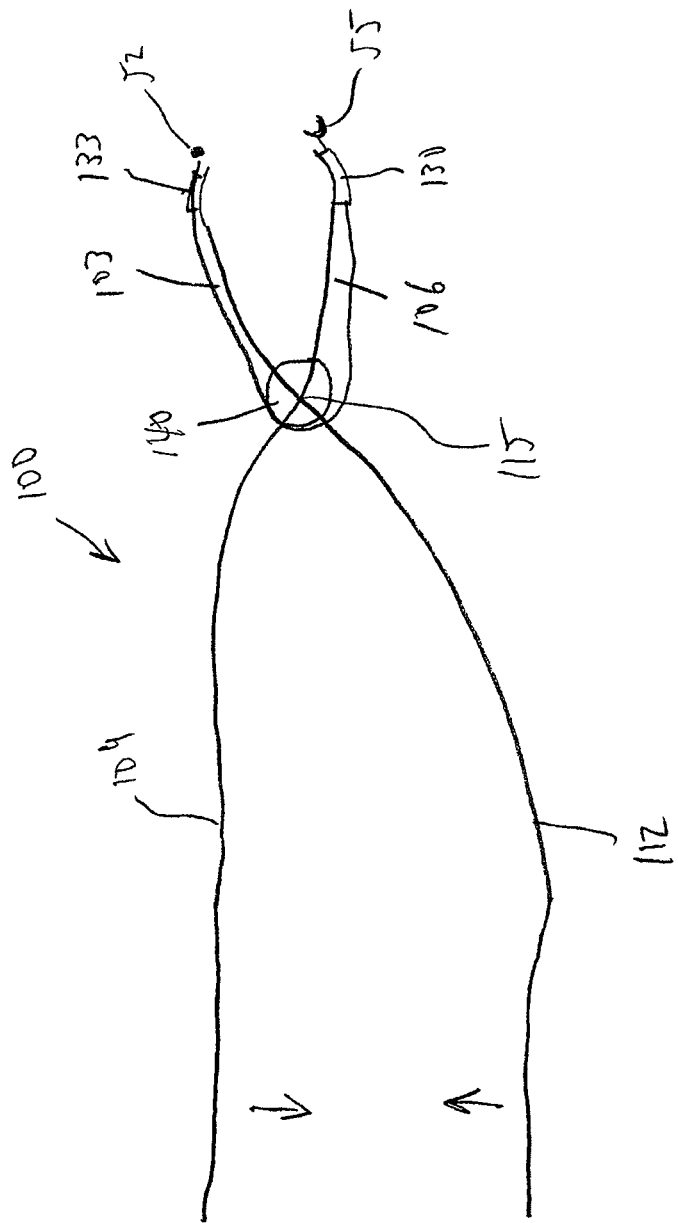
FIG. 6 is another embodiment of the insertion device.

In FIG. 6, another embodiment of the insertion device is shown. Insertion device 100 is designed with a pair of pivoting arms 103, 106 capable of holding the ends of the elastic loop apart during deployment and then bringing the ends together via scissors action by means of handles 109, 112. The two arms 103, 106 are joined at a pivot point 115. The elastic member is held in a sleeve 130 and 133 formed on the outside of the arms. A spacer member 140 at the pivot point provides a support for wrapping the elastic member in tension about the pivot. After the elastic material is deployed and the locking mechanism at each end is engaged, the insertion device can be withdrawn.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method of repairing an annulus, the method comprising:
   providing a repair device with an elastic body having a first end and a second end, one of the first and second ends having a locking mechanism disposed thereon, the repair device having first and second deployment arms removably attached to the first and second ends of the elastic body, respectively;
   stretching the elastic body;
   inserting the ends of the body through the annulus on opposite sides of a tear in the annulus;
   attaching the first end of the body to the second end of the body to form the body into a loop; and
   removing the deployment arms such that the loop contracts and the tear in the annulus is closed by the elastic body.

2. The method of claim 1, further comprising rotating at least two pivoting links disposed on the first and second deployment arms.

3. The method of claim 1, wherein attaching the first end of the body to the second end of the body comprises moving the first and second deployment arms using a pair of opposed handles pivotally connected to the first and second deployment arms.

4. The method of claim 1, wherein one of the first and second ends has a female locking member disposed thereon and one of the first and second ends has a male locking member disposed thereon.

5. The method of claim 1, further comprising moving the first and second deployment arms forward in a translatory motion using a sliding member disposed within a tube until a stop on the first or second deployment arm engages the tube.

* * * * *